US011534549B2

(12) United States Patent
Carrel et al.

(10) Patent No.: US 11,534,549 B2
(45) Date of Patent: Dec. 27, 2022

(54) ASSISTED INJECTION DEVICE FOR INJECTING A COMPOSITION CONTAINED IN A MEDICAL CONTAINER

(71) Applicant: Becton Dickinson France, Le Pont de Claix (FR)

(72) Inventors: Franck Carrel, Saint Jean de Vaulx (FR); Julien Gagliano, Grenoble (FR)

(73) Assignee: Becton Dickinson France, Le Pont de Claix (FR)

( * ) Notice: Subject to any disclaimer, the term of this patent is extended or adjusted under 35 U.S.C. 154(b) by 110 days.

(21) Appl. No.: 16/632,521

(22) PCT Filed: Jul. 20, 2018

(86) PCT No.: PCT/EP2018/069700
§ 371 (c)(1),
(2) Date: Jan. 20, 2020

(87) PCT Pub. No.: WO2019/016345
PCT Pub. Date: Jan. 24, 2019

(65) Prior Publication Data
US 2020/0188594 A1 Jun. 18, 2020

(30) Foreign Application Priority Data

Jul. 21, 2017 (EP) .................................... 17305984

(51) Int. Cl.
*A61M 5/20* (2006.01)
*A61M 5/32* (2006.01)
(Continued)

(52) U.S. Cl.
CPC .......... *A61M 5/2033* (2013.01); *A61M 5/326* (2013.01); *A61M 5/24* (2013.01);
(Continued)

(58) Field of Classification Search
CPC ...... A61M 5/2033; A61M 5/326; A61M 5/24; A61M 5/31501; A61M 5/31526;
(Continued)

(56) References Cited

U.S. PATENT DOCUMENTS 6,599,272 B1 * 7/2003 Hjertman ............ A61M 5/3156
604/209
2006/0069355 A1 * 3/2006 Judson ............... A61M 5/31511
604/211
(Continued)

FOREIGN PATENT DOCUMENTS

WO 2014029725 A1 2/2014
WO 2015059201 A1 4/2015

*Primary Examiner* — Bhisma Mehta
*Assistant Examiner* — Neeraja Gollamudi
(74) *Attorney, Agent, or Firm* — The Webb Law Firm

(57) ABSTRACT

The present disclosure relates to an assisted injection device for injecting a composition contained in a medical container. The injection device includes a body configured to receive the medical container in a fixed position relative to the body. The injection device includes a spring-loaded piston rod translationally movable inside the body along a spring axis. The injection device includes a lever pivotably mounted on the body about a first pivot axis orthogonal to the spring axis at a first distance form the spring axis. The injection device includes a selective blocking system coupled to the lever by a second pivot axis orthogonal to the spring axis. The lever is pivotable between a rest position. The selective blocking system engages the piston rod to prevent any translation movement of the piston rod and a second position wherein the selective blocking system releases the piston rod.

13 Claims, 16 Drawing Sheets

(51) Int. Cl.
*A61M 5/315* (2006.01)
*A61M 5/24* (2006.01)

(52) U.S. Cl.
CPC ... *A61M 5/31501* (2013.01); *A61M 2005/206* (2013.01); *A61M 2005/208* (2013.01); *A61M 2005/2013* (2013.01); *A61M 2005/2026* (2013.01); *A61M 2005/31508* (2013.01)

(58) Field of Classification Search
CPC ............ A61M 5/31581; A61M 5/3156; A61M 5/315; A61M 2005/2013; A61M 2005/2026; A61M 2005/206; A61M 2005/208; A61M 2005/31508; A61M 2005/2444; A61M 2005/3143; A61M 2005/2006; A61M 2005/202; A61M 2005/2073; A61M 2005/2086; A61M 5/2422; A61M 2005/3152
See application file for complete search history.

(56) References Cited

U.S. PATENT DOCUMENTS

2013/0178803 A1* 7/2013 Raab .................. A61M 5/3158
604/211
2017/0165426 A1* 6/2017 Fabien ................ A61M 5/3158

\* cited by examiner

ASSISTED INJECTION DEVICE FOR INJECTING A COMPOSITION CONTAINED IN A MEDICAL CONTAINER

CROSS-REFERENCE TO RELATED APPLICATIONS

This application is the United States national phase of International Application No. PCT/EP2018/069700 filed Jul. 20, 2018, and claims priority to European Patent Application No. 17305984.1 filed Jul. 21, 2017, the disclosures of which are hereby incorporated by reference in their entirety.

BACKGROUND OF THE INVENTION

Field

The disclosure relates to an assisted injection device for injecting a composition contained in a medical container. The injection device allows the user to control the injection by selectively allowing or stopping the injection, and makes the injection easier for a user who needs to provide less effort for injecting the composition, especially a composition with a high viscosity, as well as controlling the injection rate while performing the injection.

Background Art

Prefilled injection devices are common containers to deliver drugs or vaccines to patients and include syringes, cartridges and autoinjectors or the like. They usually comprise a sealing stopper in gliding engagement into a container, the container being filled with a pharmaceutical composition in order to provide the practitioners with a ready-to-use injection device for patients.

A container has a substantially cylindrical shape, and comprises a proximal end able to be stoppered by a sealing stopper, a distal end wherein the pharmaceutical composition is expelled from the container, and a lateral wall extending between the proximal end and the distal end of the container. In practice, the sealing stopper is aimed at moving, upon the pressure exerted by a piston rod, from a proximal end of the container towards the distal end of the container, thereby expelling the drug contained into the container.

When compared to empty injection devices that are filled with a vial-stored pharmaceutical composition just prior to the injection to the patient's body, the use of prefilled injection devices leads to several advantages. In particular, by limiting the preparation prior to the injection, the prefilled injection devices provide a reduction of medical dosing errors, a minimized risk of microbial contamination and an enhanced convenience of use for the practitioners. Furthermore, such prefilled containers may encourage and simplify self-administration by the patients which allows reducing the cost of therapy and increasing the patient adherence. Finally, prefilled injection devices reduce loss of valuable pharmaceutical composition that usually occurs when a pharmaceutical composition is transferred from a vial to a non-prefilled injection device. This results in a greater number of possible injections for a given manufacturing batch of pharmaceutical composition thus reducing buying and supply chain costs.

In certain cases, the injection of the pharmaceutical composition contained in the container with a manual injection device, such as a syringe, can be difficult to carry out, due to the force that needs to be applied onto the piston rod for expelling it. This occurs for example when the pharmaceutical composition has a high viscosity, and/or when the injection is carried out manually by a user that cannot push on the piston rod strongly enough with his fingers, for example when suffering from rheumatoid arthritis or from any type of disease affecting the user's hand or fingers. The injection may be a self-injection or may be performed by a user, such as a health care professional, to another person. In the case of healthcare professionals performing repetitive injections of viscous drugs to patients, the repetition of the same gesture requiring high force applied on the plunger rod to make the injection may cause repetitive strain injuries.

Autoinjectors can assist the user in performing an automatic injection of the pharmaceutical composition. They usually comprise an injection button the user needs to press in order to start the injection.

The injection carried out with an autoinjector is automatic, which means that once the user has pressed the injection button to move the piston, the injection starts and keeps going until the entirety of the pharmaceutical composition is injected.

A consequence is that once the user has triggered the injection by pushing the button, the injection cannot be stopped and restarted again. In particular, carrying out multiple injection sequences of fractions of the pharmaceutical composition while stopping the injection between two consecutive sequences is also not possible.

Moreover, the user cannot change the injection rate (or injection speed) while performing the injection with an autoinjector. In other terms, it is not possible to increase or decrease the injection rate while performing the injection.

This lack of control of the injection can generate pain and anxiety to the user, and may lead the user to be unable to perform the injection correctly.

Moreover, similarly to manual injection devices, autoinjectors can encounter difficulties for injecting a pharmaceutical composition with a high viscosity, mainly due to an insufficient force applied to the piston by the injection mechanism. Hence, the pharmaceutical composition is not expelled from the container, or at most expelled at a very low speed.

SUMMARY

In view of the foregoing, there is a strong need for an injection device for injecting a pharmaceutical composition contained in a medical container which allows the user to control the injection, in particular to stop the injection then starting it again and to adjust the injection rate while performing the injection. There is also a need for such an injection device that allows for an easier injection of the pharmaceutical composition compared to the existing injection devices, in particular when the pharmaceutical composition has a high viscosity and/or when the user has a reduced physical strength.

An object of the disclosure is thus to provide an assisted injection device for injecting a pharmaceutical composition contained in a medical container that overcomes the drawbacks of the known devices.

Such an improved device allows for assisting the user for carrying out easy injection of the pharmaceutical composition contained in the container as well as controlling the injection.

One object of the disclosure is an assisted injection device for injecting a composition contained in a medical container, comprising:

a body configured to receive the medical container in a fixed position relative to the body, a spring-loaded piston rod translationally movable inside the body along a spring axis, between a proximal rest position and a distal operative position wherein the piston rod engages a stopper of the medical container and pushes the stopper in the medical container, a lever pivotably mounted on the body about a first pivot axis orthogonal to the spring axis at a first distance from the spring axis, comprising an actuation zone configured to be pressed on by a user, said actuation zone being opposite the first pivot axis relative to the spring axis, at a second distance from the spring axis, a selective blocking system coupled to the lever by a second pivot axis orthogonal to the spring axis, the lever being pivotable between a rest position wherein the selective blocking system engages the piston rod to prevent any translational movement of the piston rod and a second position wherein the selective blocking system releases the piston rod to allow the piston rod to move toward the distal operative position under the spring force.

In this application, the "distal direction" is to be understood as meaning the direction of injection, with respect to the medical container the device of the disclosure is to be mounted on. The distal direction corresponds to the travel direction of the plunger rod during the injection, the pharmaceutical composition contained initially in the medical container being expelled from said medical container. The "proximal direction" is to be understood as meaning the opposite direction to said direction of injection.

In this application, the term "orthogonal" designates two axes—extending in a three-dimensional space—that are parallel to respective axes that intersect at a right angle. Said orthogonal axes may belong to a same plane and thus intersect (in this case they are perpendicular), or not.

According to other optional features of the device of the disclosure:

the second distance is greater than the first distance, preferably at least two times greater than the first distance;

the second pivot axis intersects the spring axis;

the piston rod is provided with a toothed rack that extends along its outer wall, and the selective blocking system comprises:
a rotatably movable wheel comprising:
a first part being a rotatably movable cogwheel, including teeth adapted to mesh with the toothed rack of the piston rod,
a second part coaxial with the first part (76) and rotatably movable with the first part, comprising a curved surface,
a connecting rod including a first end coupled to the lever by the second pivot axis and a second end provided with a hole that receives the second part of the wheel, the connecting rod being movable by the lever between a first position wherein the lever is in the rest position and the inner surface of the hole engages the curved surface of the second part of the wheel so as to block the wheel by friction thereby blocking the piston rod, and a second position wherein the lever is the operative position and the inner surface of the hole disengages the curved surface of the second part of the wheel so as to allow the rotation of the wheel thereby allowing the piston rod to move;

the ratio of the diameter of the first part of the wheel to the diameter of the second part of the wheel is preferably comprised between 2 and 3;

the curved surface of the second part of the wheel is made of at least one of epoxy resin, plastic material, steel, aluminum, or rubber and the inner surface of the hole of the connecting rod is made of at least one of epoxy resin, plastic material, steel, or rubber;

the piston rod is provided with a toothed rack that extends along its outer wall, and the selective blocking system comprises:
a pawl comprising a surface provided with a at least one tooth,
a connecting rod assembly including a first end coupled to the lever by the second pivot axis, and a second end coupled to the pawl, the connecting rod assembly being movable by the lever between a first position wherein the lever is in the rest position and the pawl meshes with the toothed rack of the piston rod so as to block the piston rod, and a second position wherein the lever is in the operative position and the pawl disengages the toothed rack of the piston rod so as to allow the piston rod to move.

the body comprises a container holder system configured to receive at least a portion of the medical container and to hold the medical container aligned with the movement direction of the piston rod so that when moving from the proximal rest position to the distal operative position, the piston rod engages the stopper of the medical container and pushes the stopper in the medical container to inject the composition;

the container holder system comprises:
an opening provided in the distal wall of the body that leads to a housing adapted to receive at least a portion of the medical container in a position aligned with the movement direction of the piston rod,
a slot provided in the outer wall of the body that leads to the housing,
an insert adapted to be inserted in the slot to contact the medical container and to maintain the medical container in a fixed position in the housing;

the container holder system comprises:
a slot provided in the outer wall of the body that leads to a housing, configured to receive at least a portion of the medical container and to maintain the medical container in a fixed position aligned with the movement direction of the piston rod,
a through groove provided in the distal wall of the body, continuous with the slot and extending in the distal wall from the slot, the groove being configured to guide the medical container inserted via the slot to the housing;

the device is handheld, i.e. is configured to be carried in one hand of a user during use and transport from one location to another. The dimensions and the weight of the device are advantageously adapted for this purpose.

BRIEF DESCRIPTION OF THE DRAWINGS

Further features and advantages of the disclosure will become apparent from the detailed description to follow, with reference to the appended drawings, in which:

FIGS. 1A and 1B are respectively bottom and top views of the injection device illustrated in FIG. 1;

DETAILED DESCRIPTION

The disclosure proposes an assisted injection device for injecting a composition contained in a medical container.

Prior to the injection, the medical container is filled with the composition intended to be injected, and stoppered with a stopper inserted therein. The stoppered medical container is then mounted on the device to constitute an injection assembly, and the injection of the composition can be carried out.

Figure 1:
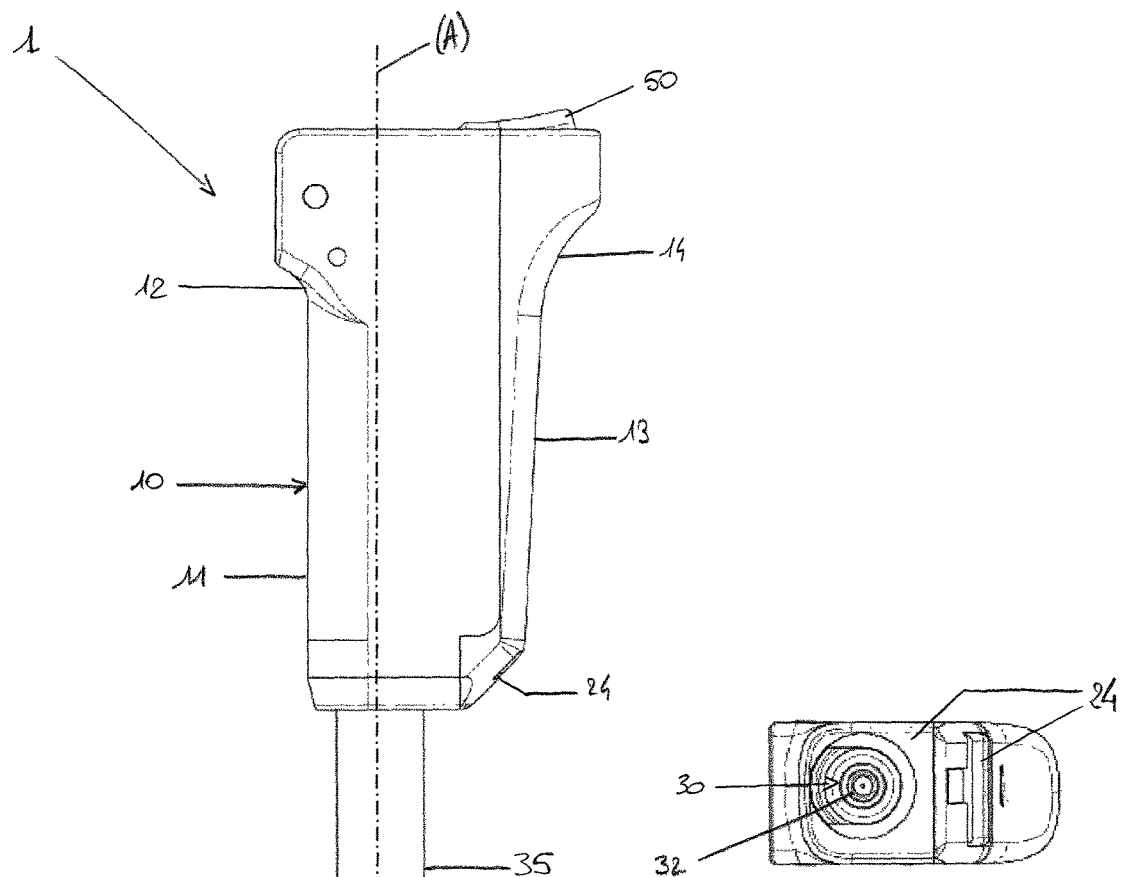
FIG. 1 is a side view of an embodiment of the injection device of the disclosure.
Figure 1:
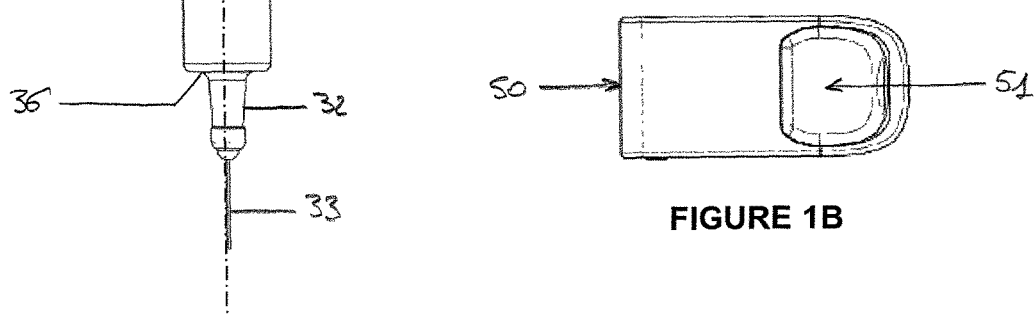
Figure 2:
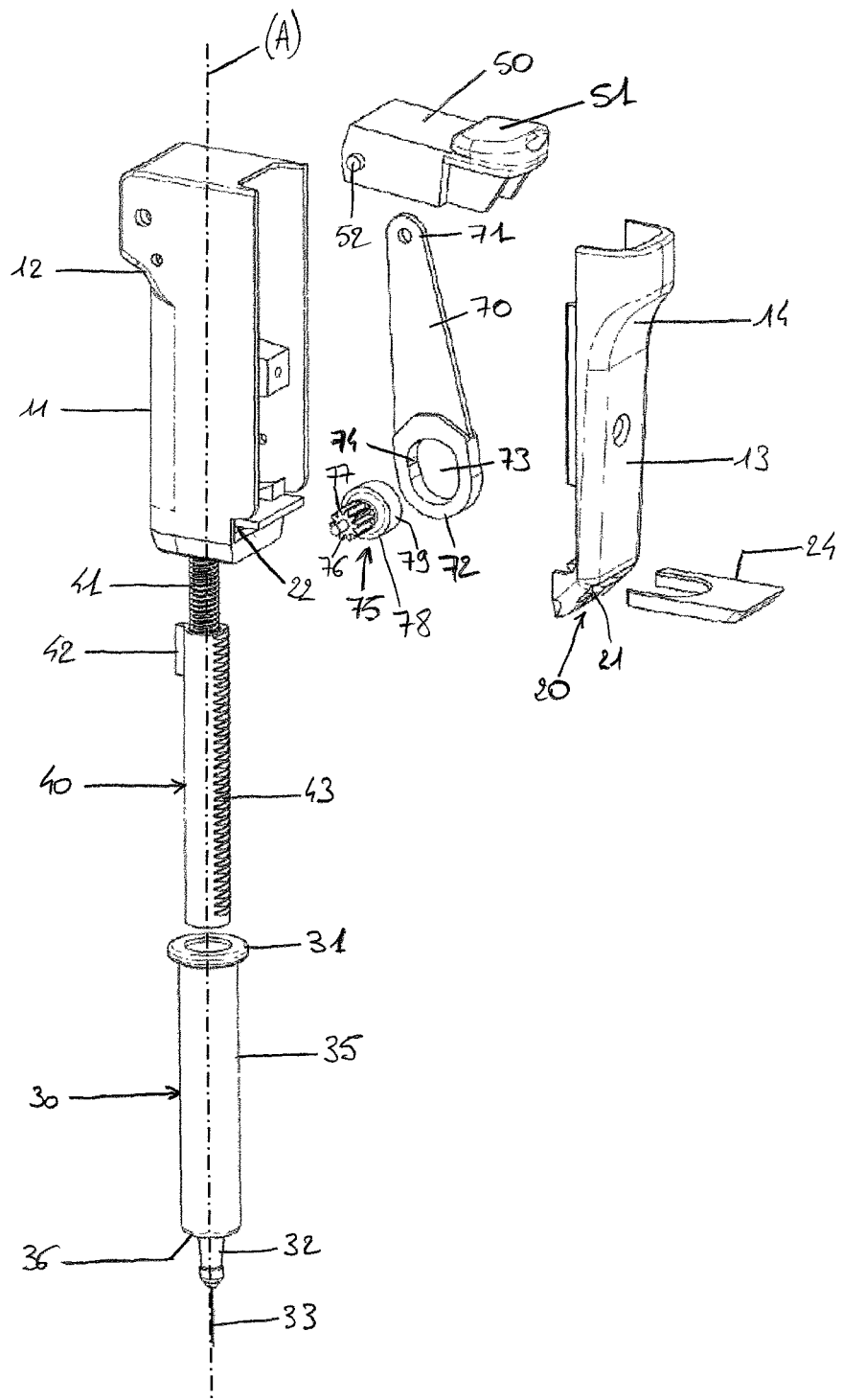
FIG. 2 is an exploded perspective view of the components of the injection device, the device comprising a selective blocking system according to a first embodiment.

In reference to FIGS. 1 and 2, the assisted injection device 1 comprises a body 10 adapted to be held by a user's hand. To this end, the front side of the body is provided with a front grip surface 11 limited proximally by a flared portion 12 of the body that extends radially outwardly. Similarly, the rear side of the body is provided with a rear grip surface 13 limited proximally by a flared portion 14 of the body that extends radially outwardly. Hence, when using the device 1, the user can easily grab the body 10 so that his fingers and palm contact the front and rear grip surfaces 11, 13 respectively and the lateral side of his hand abuts the flared portions 12, 14, thus facilitating the handling of the device.

The medical container comprises a body 35 including a proximal end 31, and a distal end having a tip 32 and a needle 33 extending from thereon. The needle 33 may be covered by a cap (not represented) to prevent any injury when handled before use.

The body 10 comprises a container holder system 20.

Figure 3A:
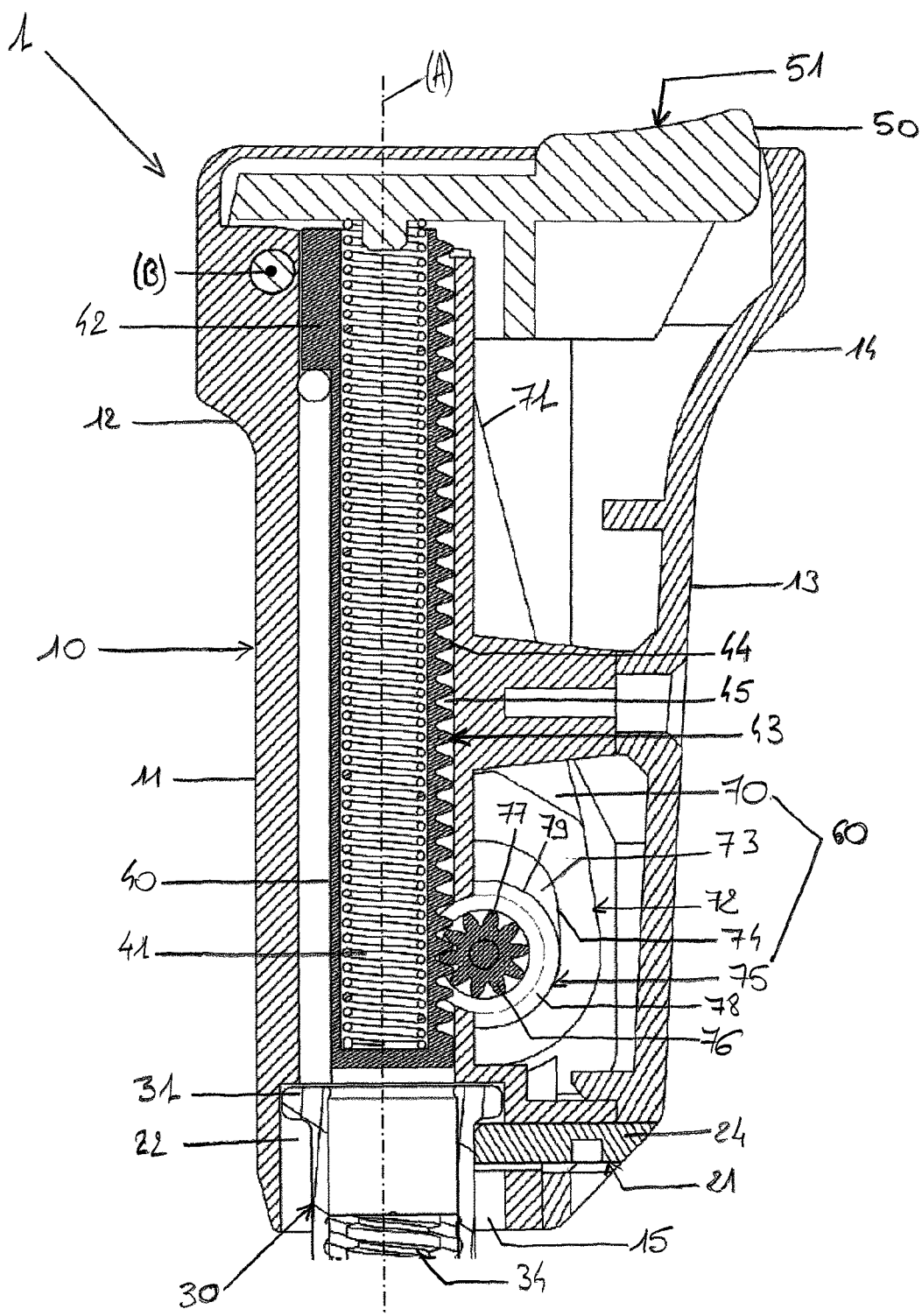
FIGS. 3A and 3B are side sectional views from a first side of the device, wherein the selective blocking system according to the first embodiment respectively blocks and allow the movement of the piston rod.
Figure 3B:
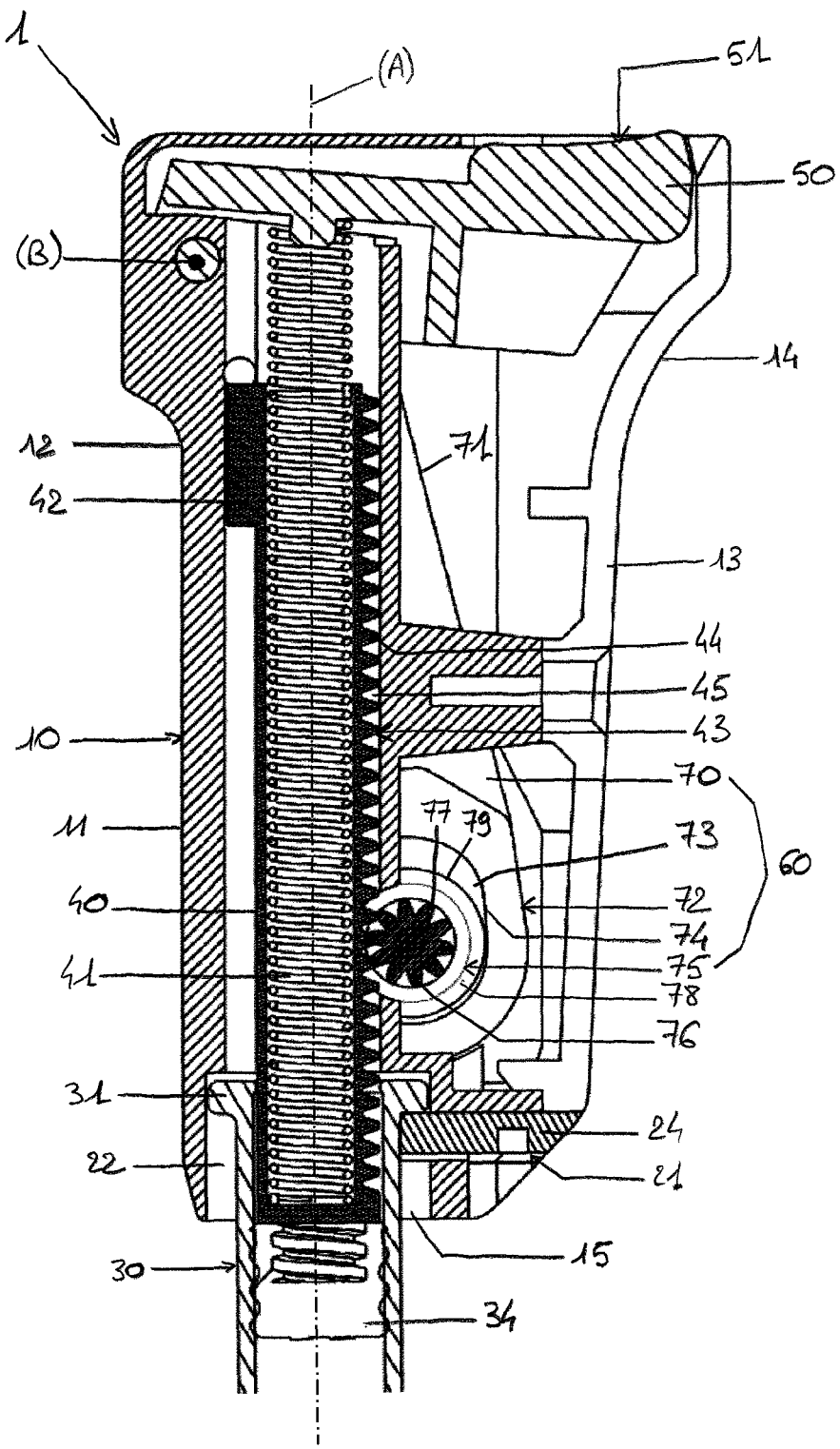

According to a first embodiment illustrated on FIGS. 2 and 3A-B, the container holder system includes an opening 15 provided in the distal end of the body 10 that leads to a housing 22 adapted to receive the proximal end 31 of the medical container 30. The container holder system further includes a slot 21 provided in the outer wall of the body 10 in communication with the housing, and an insert 24 adapted to be inserted into the slot 21 until coming into contact with the proximal end 31 of the medical container 30 for securing it in the housing 22. The insert 24 is shown inserted in the slot 21 in FIG. 1A and out of the slot in FIG. 2. The insert is advantageously in the form of a fork with two branches so as to grip the body 35 of the container inserted in-between. The proximal end of the container then abuts the insert 24 thereby avoiding the container to fall off the device.

In a practical way, the proximal end of the container 30 is inserted through the opening 15 and moved longitudinally in a proximal direction along an axis (A) until being positioned in the housing 22 and the insert 24 is then inserted radially in the slot 21 to secure the medical container 30 in a fixed position relative to the body 10.

This embodiment is particularly useful when the container 30 is a syringe or the like as the proximal end of the container 30 is a flange adapted to abut the insert 24.

Figure 11:
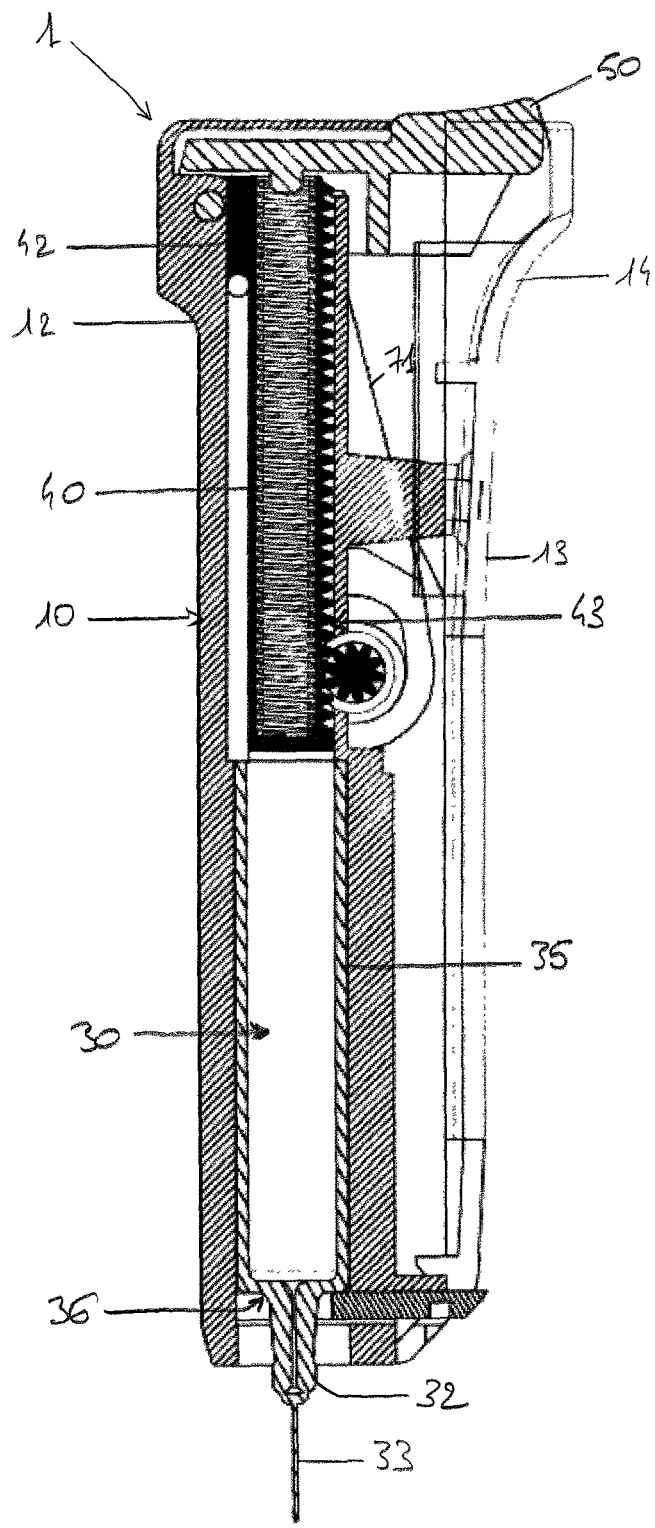
FIG. 11 is a side sectional view of the device including a container holder system according to a first embodiment.

Alternatively, when the container 30 is a cylinder or the like (with no proximal flange), the configuration of the container holder system of the first embodiment may be adapted accordingly. According to an embodiment illustrated in FIG. 11, the housing 22 extends distally in a portion of the body 10 of the device, and is configured to receive the entire body 35 of medical container 30. Advantageously, in this situation, only the tip 32 and a needle 33 of the medical container 30 project distally out of the body 10 of the device. Of course, this embodiment may also be appropriate when the medical container 30 is a syringe or the like, the housing 22 being adapted accordingly to accommodate the flange of the medical container.

In a practical way, the proximal end of the container 30 is inserted in the housing 22 through a lateral opening (not represented) provided in the peripheral surface of the body 10. To that end, the dimensions of the lateral opening correspond substantially to the dimensions of the body 35 of the medical container 30. The insert 24 is then inserted in the slot 21 until being in contact with a shoulder 36 extending between the distal end of the body 35 and the tip 32 of the medical container 30. Hence, the shoulder 36 abuts the insert 24, which thereby maintains the container 30 in a fixed position in the housing 22.

Figure 12:
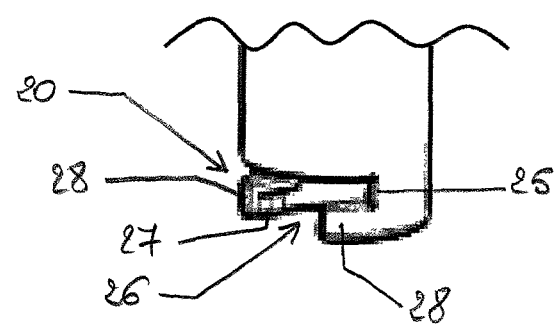
FIG. 12 is a perspective view of the container holder system of the device according to a second embodiment.

According to a second embodiment illustrated on FIG. 12, the container holder system 20 includes a slot 25 provided in the outer wall of the body 10 that leads to a housing 26 adapted to receive the proximal end 31 of the medical container 30.

The container holder system 20 further includes a through groove 27 provided in the distal wall of the body 10, continuous with the slot 25 and extending in the distal wall from the slot 25. In a practical way, the proximal end of the container 30 is inserted through the slot 25 and moved in a radial direction along the groove 27 until being positioned in the housing 26 where the medical container 30 is maintained in a fixed position relative to the body 10. The groove 27 separates two projecting parts 28 against which the proximal end of the medical container can abut, thereby preventing the container from falling off the groove.

To this end, the inner surface of the groove 27 contacts the body 35 of the container 30. In particular, the groove 27 can be configured to prevent the container 30 inserted herein from moving radially, unless the container is moved by a user. The groove is preferably made of a rigid and smooth material, such as rigid plastic or metal (e.g aluminum, stainless steel) for example, for making the insertion of the container therein easier, as well as contributing to maintain the container in a fixed position in the housing 26 during the injection.

This embodiment is particularly useful when the container 30 is a syringe or the like as the proximal end of the container 30 is a flange adapted to abut the projecting parts.

Alternatively, when the container 30 is a cylinder or the like (with no proximal flange), the configuration of the container holder system of the second embodiment may be adapted accordingly.

The dimensions of the slot are adapted to receive the entire body 35 of the medical container 30 inserted therein, while the tip 32 of the container 30 is moved in a radial direction along the groove 27 until being positioned in the housing 26 where the medical container 30 is maintained in a fixed position relative to the body 10. When the container 30 is positioned in the housing 26, the shoulder 36 abuts the projecting parts 28 thereby avoiding the medical container to fall off the device.

The injection device 1 comprises a piston rod 40 that extends inside the body 10 along a longitudinal axis (A). A spring 41 is arranged inside the body 10, coaxially and in contact with the piston rod 40. The container 30 maintained in the container holder system 20 is aligned with the axis (A), called spring axis. In that way, the spring-loaded piston rod 40 is translationally movable inside the body 10 under the force of the spring 41 along the axis (A), between a proximal rest position and a distal operating position wherein the piston rod 40 engages the stopper 34 of the medical container 30 and pushes said stopper into the medical container.

The piston rod 40 comprises advantageously a radially enlarged proximal end 42 that serves as a mechanical stop. At the end of the injection, the enlarged proximal end 42 abuts the proximal end of the medical container 30, thus avoiding the piston rod 40 to fall off from the body 10.

The piston rod 40 is provided with a toothed rack 43 that extends along its outer wall. The toothed rack 43 is provided with a plurality of teeth 44 oriented radially, and two consecutive teeth are separated by a notch 45.

A lever 50 is pivotably mounted on a proximal side of the body 10 about a first pivot axis (B) orthogonal to the spring axis (A) and at a first (non-zero) distance from the spring axis (A). An actuation zone 51 is provided on the lever 50, opposite the pivot axis (B) relative to the spring axis (A). The actuation zone 51 is located at a second (non-zero) distance from the spring axis (A). The actuation zone 51 is integral with the lever 50 and constitutes a button configured to be pressed on by the user, in particular in a distal direction, in order to move the lever 50 in a tilting motion about the pivot axis (B), from a first position called "rest position" to a second position. The proximal end of the spring 41 is preferably fixed to the lever 50, but can alternatively be fixed directly to the body 10 of the device.

The injection device 1 further comprises a selective blocking system 60 for selectively blocking or releasing the piston rod 40.

According to a first embodiment of the selective blocking system 60 illustrated in FIGS. 2, 3A-B, 4A-B, 5, and 6, the selective blocking system comprises a connecting rod 70 including a proximal end 71 pivotably coupled to the lever 50 via a stud 52 provided in the lateral surface of the lever 50 that extends from thereon about a second pivot axis (C) orthogonal to the spring axis (A), and preferably intersecting the axis (A).

The distal end 72 of the connecting rod 70 is provided with a hole 73 of a substantially oblong shape.

The selective blocking system further comprises a two-part wheel 75.

The first part 76 of the wheel 75 is a cogwheel rotatably movable around its rotation axis, including teeth 77 adapted to mesh with the toothed rack 43 of the piston rod 40 thereby forming a gear. Hence, a translational movement of the piston rod 40 induces a corresponding rotation of the wheel 75 and vice versa.

The second part 78 of the wheel 75 is rotationally movable with the first part 76, and preferably coaxial with the first part. The second part 78 is advantageously integral with the first part 76. The second part 78 is positioned in the hole 73 of the connecting rod 70, and comprises a curved surface 79 adapted to contact the inner surface 74 of the hole 73 of the connecting rod 70, so as to block the wheel 75 by friction of said surfaces. The radius of curvature of the second part 78 of the wheel may be adjusted depending on the radius of curvature of the inner surface 74 of the hole of the connecting rod (to ensure a sufficient contact surface between the wheel 75 and the connecting rod 70), depending on the materials of the second part 78 of the wheel and the connecting rod 70 and/or the surface condition thereof (to adjust their coefficient of friction), and depending on the spring force of the spring 41 (so that the friction force is greater than the spring force). The ratio of the diameter of the first part 76 of the wheel to that of the second part 78 of the wheel, and conversely, may also be adjusted according to the features above. For example, this ratio may be comprised between 2 and 3, and is preferably equal to about 2.

The curved surface 79 and the inner surface 74 of the hole 73 may be made of the same material, or different materials, selected from: epoxy resin, plastic material, steel, aluminum, or rubber.

By selectively pushing or releasing the actuation zone 51 of the lever 50, the user can start or stop the injection of the pharmaceutical composition contained in the medical container.

Figure 4A:
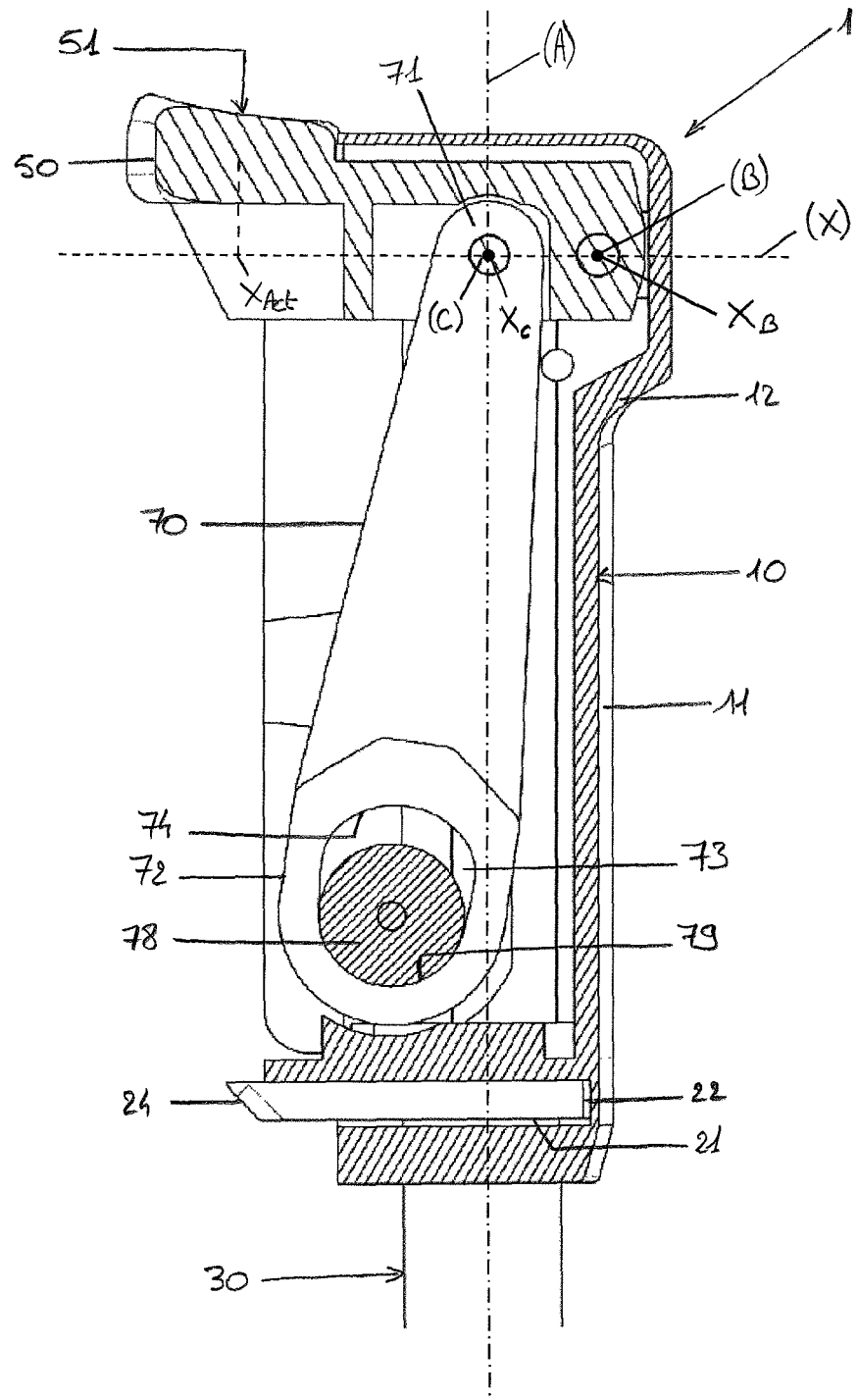
FIGS. 4A and 4B are side sectional views from a second side of the injection device, wherein the selective blocking system according to the first embodiment respectively blocks and allow the movement of the piston rod.

As illustrated in FIGS. 3A and 4A, when the actuation zone 51 is released, the lever 50 is in a rest position. The curved surface 79 of the second part of the wheel contacts the inner surface 74 of the hole of the connecting rod 70, thereby blocking the wheel 75 with a friction force equal to or greater than the spring force. As the cogwheel is blocked, the piston rod 40 is also blocked. In this rest position, the spring 41 is compressed.

Figure 4B:
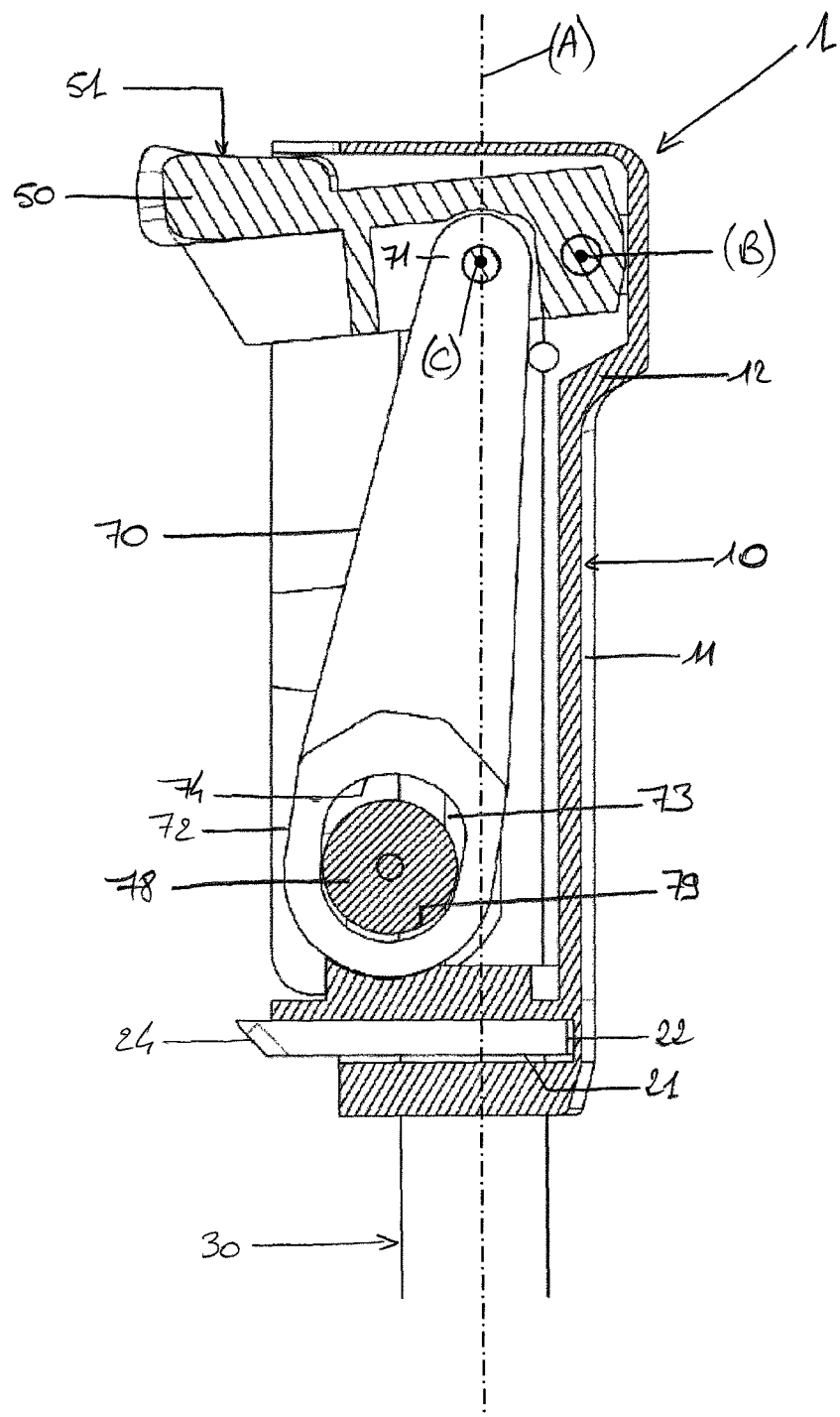
Figure 5:
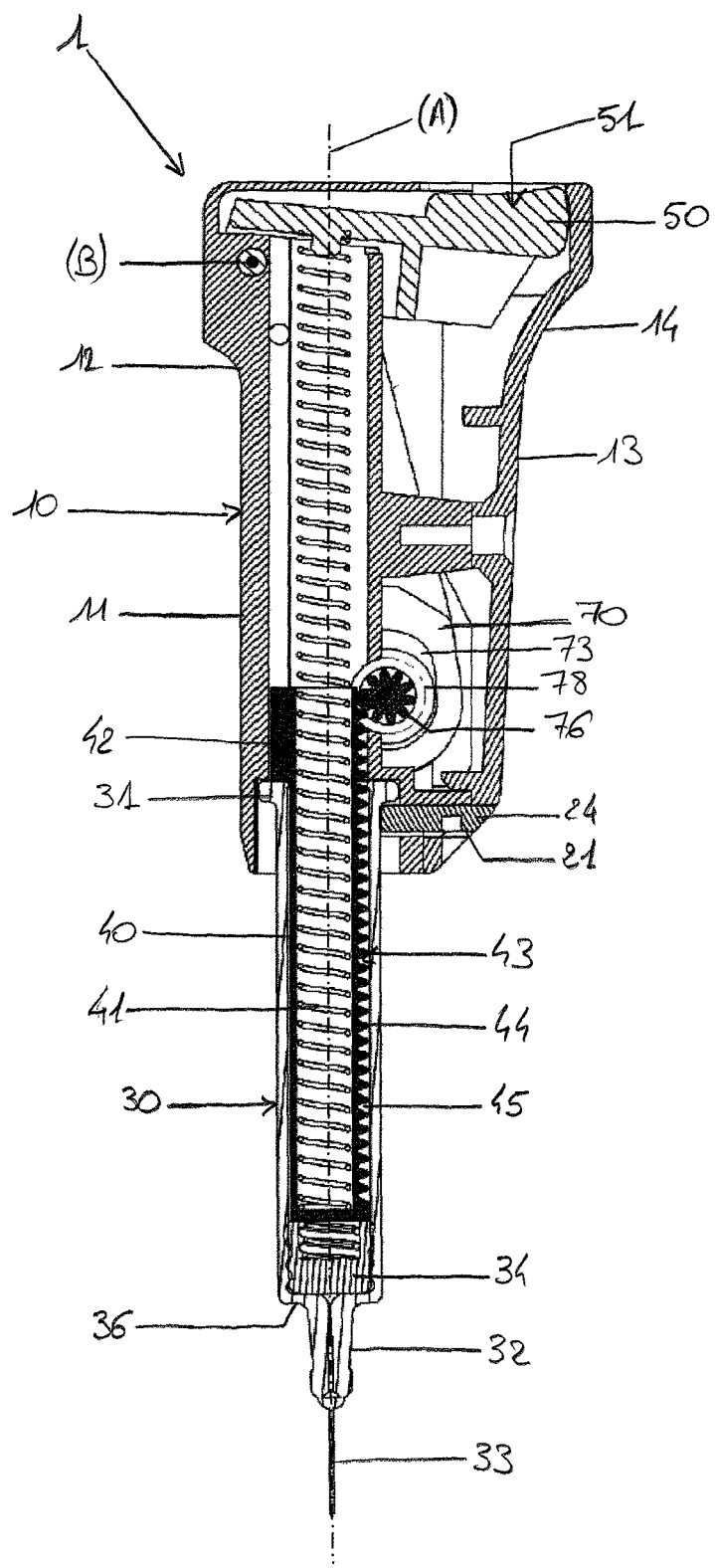
FIG. 5 is a side sectional view from a first side of the injection device illustrated in FIGS. 3A, 3B, 4A, 4B, wherein the injection is finished and the entirety of the pharmaceutical composition has been expelled from the medical container.
Figure 6:
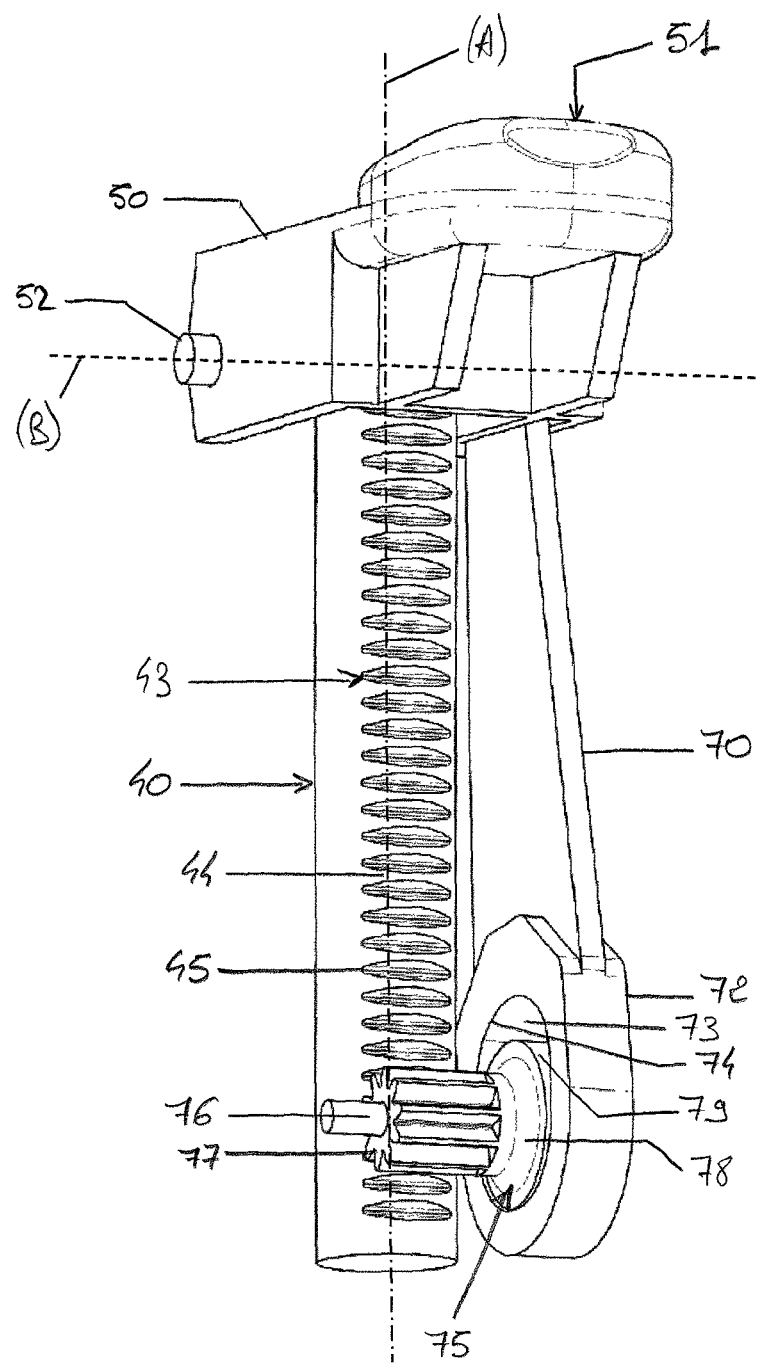
FIG. 6 is a perspective view of the selective blocking system of the injection device, according to the first embodiment.
Figure 7:
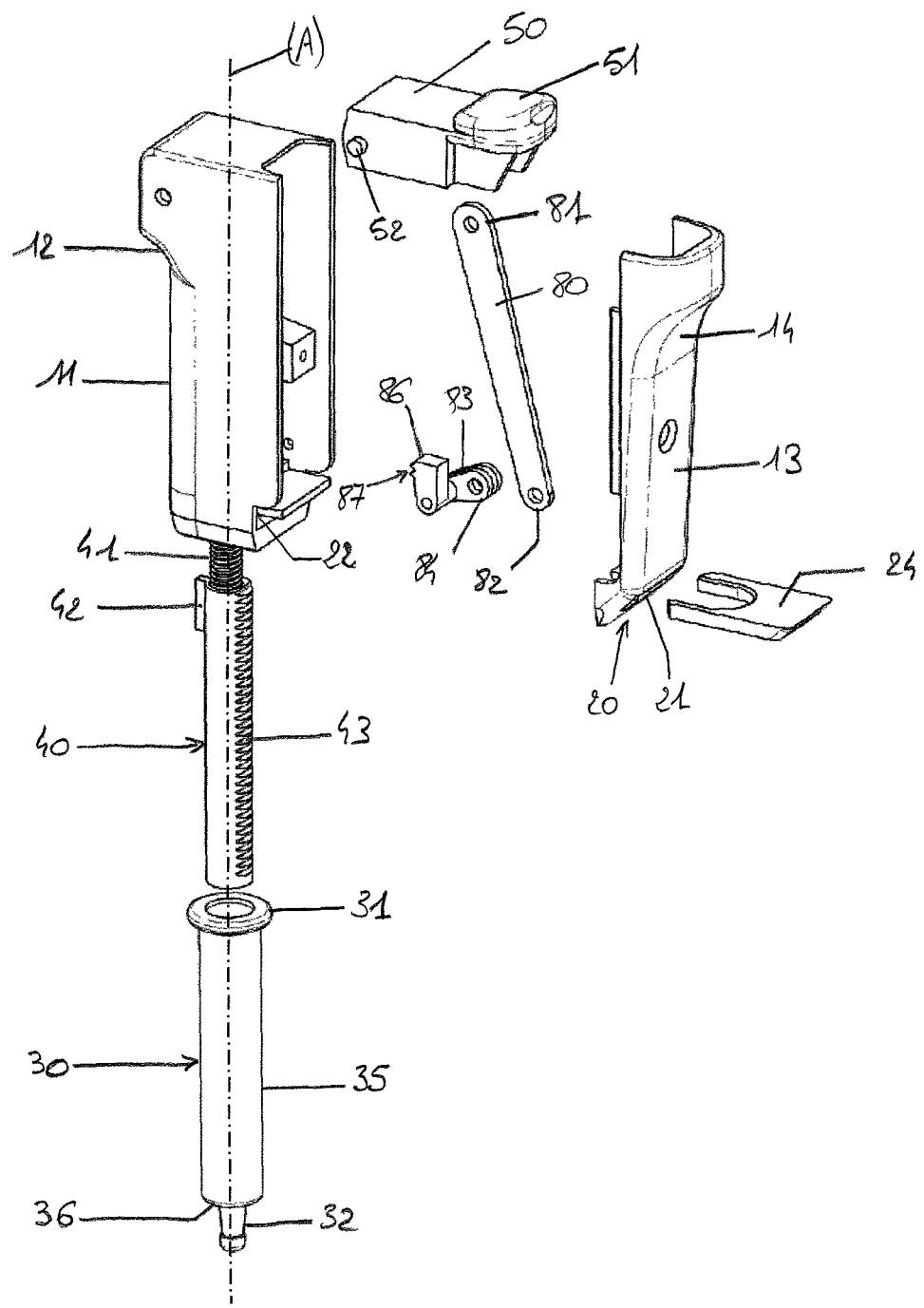
FIG. 7 is an exploded perspective view of the components of the injection device, the device comprising a selective blocking system according to a second embodiment.

As illustrated in FIGS. 3B and 4B, when the user pushes the actuation zone 51 in a distal direction, the lever 50 moves in a tilting motion about the pivot axis (B) and pushes the connecting rod 70 in a distal direction. Due to the movement of the connecting rod, the curved surface 79 of the second part 78 of the wheel disengages the inner surface 74 of the hole 73 of the connecting rod 70, thereby allowing the rotation of the wheel 75 and allowing the piston rod 40 to move translationally with the spring force of the spring 41 in a distal direction, to a distal operative position wherein the piston rod 40 engages the stopper 34 and pushes said stopper in the medical container 30. The composition is thus expelled from the medical container. In this position, the spring 41 is at least partially released.

As long as the user keeps pushing the actuation zone 51, the connecting rod 70 remains in a distal position, the curved surface 79 of the second part 78 of the wheel 75 remains disengaged from the inner surface 74 of the hole 73 of the connecting rod 70, the piston rod 40 keeps moving with the release of the spring 41, and the injection continues.

During injection, when the user releases the actuation zone 51, the lever 50 moves back in a tilting motion to its rest position thanks to the spring force of the spring 41, the second part of the wheel 75 reengages the inner surface 74 of the hole of the connecting rod 70, and the device 1 returns in the situation described previously, the piston rod 40 being in a more distal position than previously.

As such, the user can start or stop the injection simply by pressing the actuation zone 51 during a certain amount of time or by releasing it.

Moreover, the user can adapt and vary the intensity of the friction force between the wheel 75 and the connecting rod 70 while performing the injection, simply by pushing the actuation zone 51 harder or lighter, thereby adjusting the speed of the piston rod 40 and the injection rate accordingly. In more details, the harder the user pushes the actuation zone 51, the lower the intensity of the friction force, and the greater the injection rate. Conversely, the less the user pushes the actuation zone 51, the greater the intensity of the friction force, and the lower the injection rate.

For example, the user can push the actuation zone 51 and maintain the same force for a given amount of time to inject the composition. The user can then progressively push the actuation zone 51 harder so as to accelerate the injection gradually (for example when the volume of the composition to be injected is important) or alternatively he can partially and progressively release the actuation zone 51 so as to slow down the injection gradually (for example when the injection is painful or when the user is anxious).

According to a second embodiment of the selective blocking system 60 illustrated in FIGS. 7, 8A-B, 9A-B, and 10, the selective blocking system comprises a connecting rod 80 including a proximal end 81 pivotably coupled to the lever 50 via the stud 52 provided in the lateral surface of the lever 50 that extends from thereon about a pivot axis (C) orthogonal to the spring axis (A), and preferably intersecting the axis (A).

The selective blocking system further comprises a pawl 86 coupled to one end 85 of a secondary connecting rod 83, preferably spring-biased. The other end 84 of the secondary connecting rod 83 is pivotably mounted to the distal end 82 of the connecting rod 80.

The pawl 86 is provided with at least one tooth 87, possibly a row of teeth, on its lateral surface, configured to mesh with the toothed rack 43 to form a ratchet.

Figure 8A:
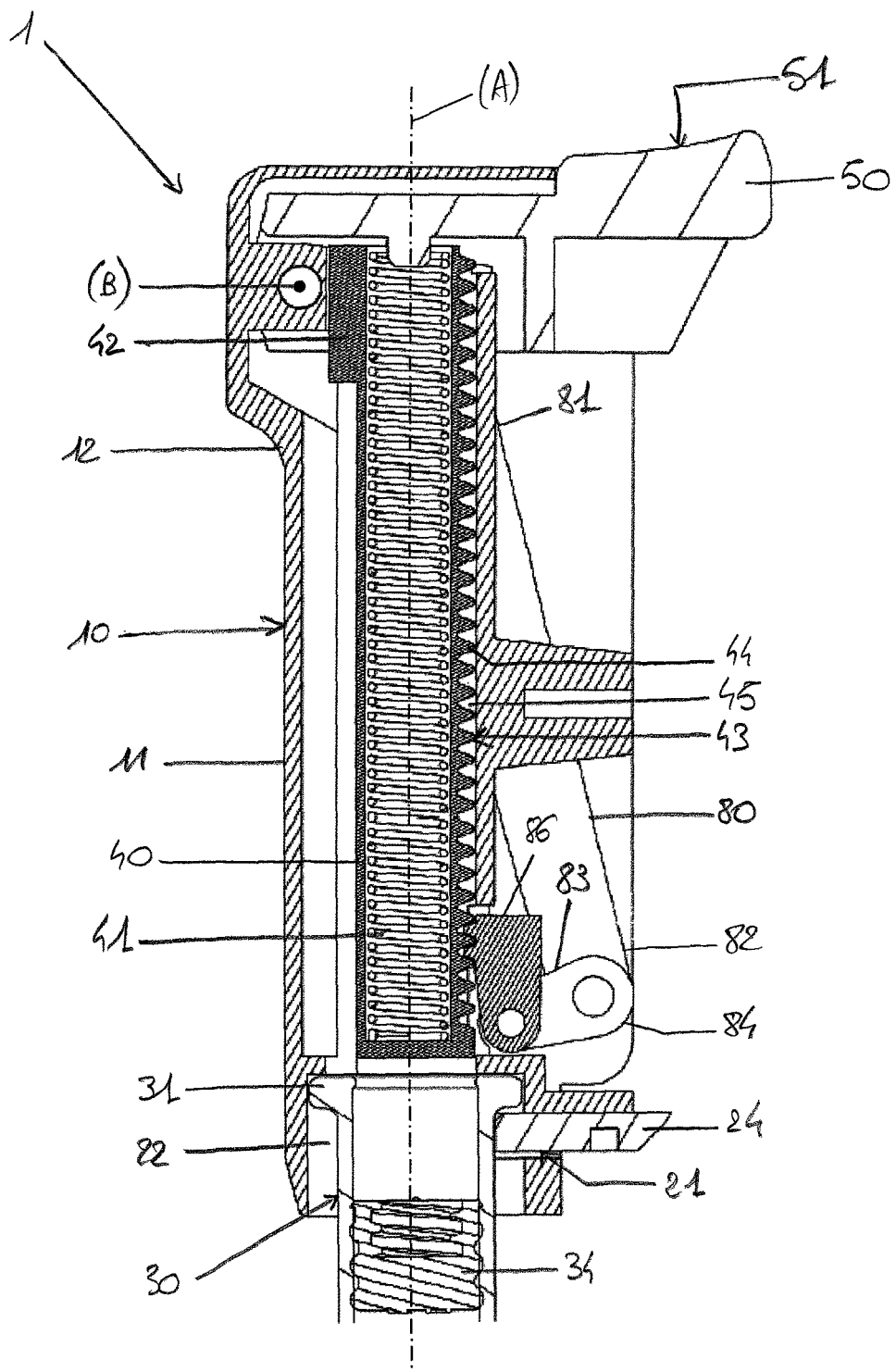
FIGS. 8A and 8B are side sectional views from a first side of the injection device, wherein the selective blocking system according to the second embodiment respectively blocks and allow the movement of the piston rod.
Figure 9A:
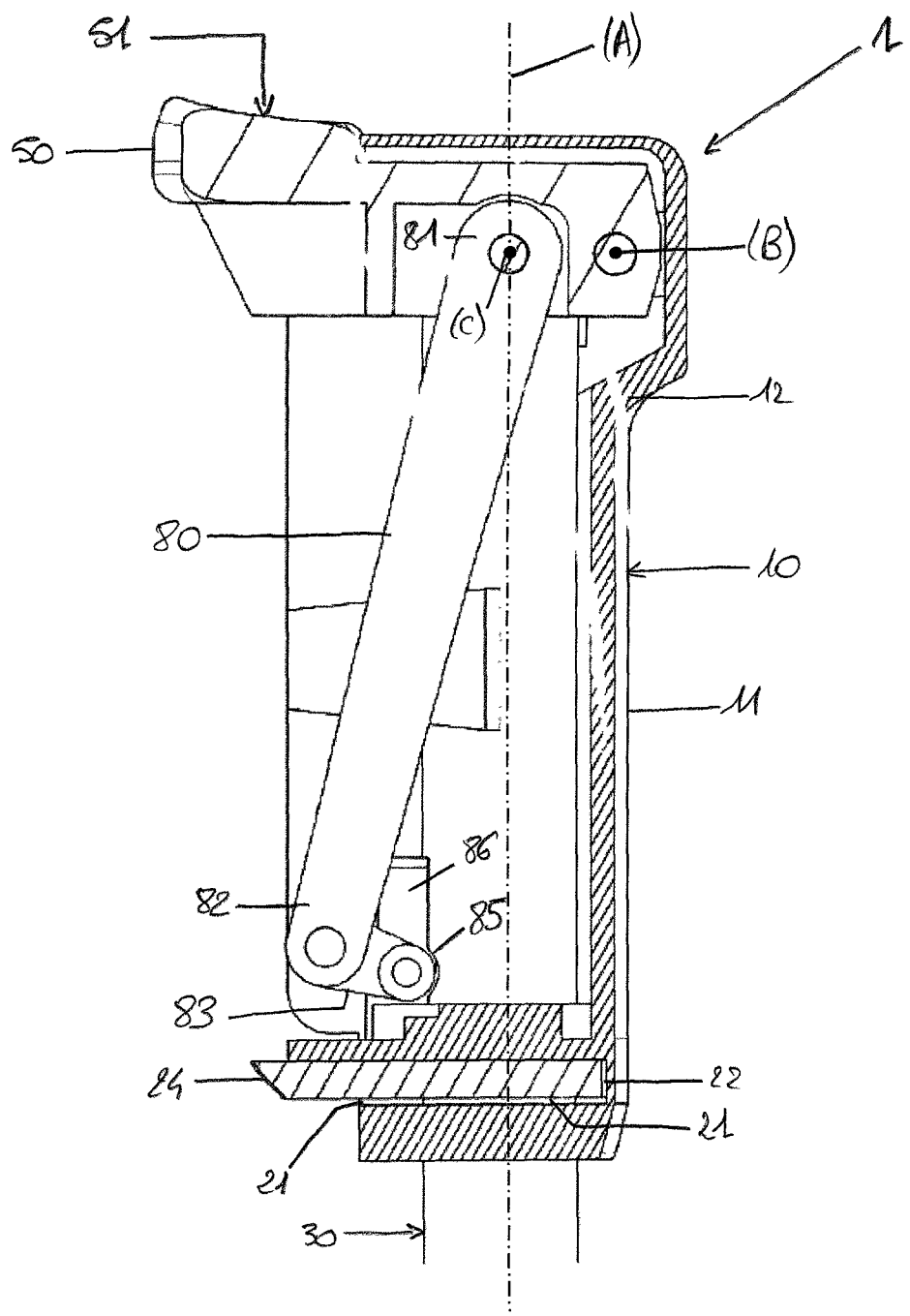
FIGS. 9A and 9B are side sectional views from a second side of the device illustrated in FIG. 1, wherein the selective blocking system according to the second embodiment respectively blocks and allow the movement of the piston rod.

As illustrated in FIGS. 8A and 9A, when the actuation zone 51 is released, the lever 50 is in a rest position.

The toothed pawl 86 meshes with the toothed rack 43 of the piston rod 40, thereby blocking the piston rod 40 and maintaining the spring 41 compressed.

Figure 8B:
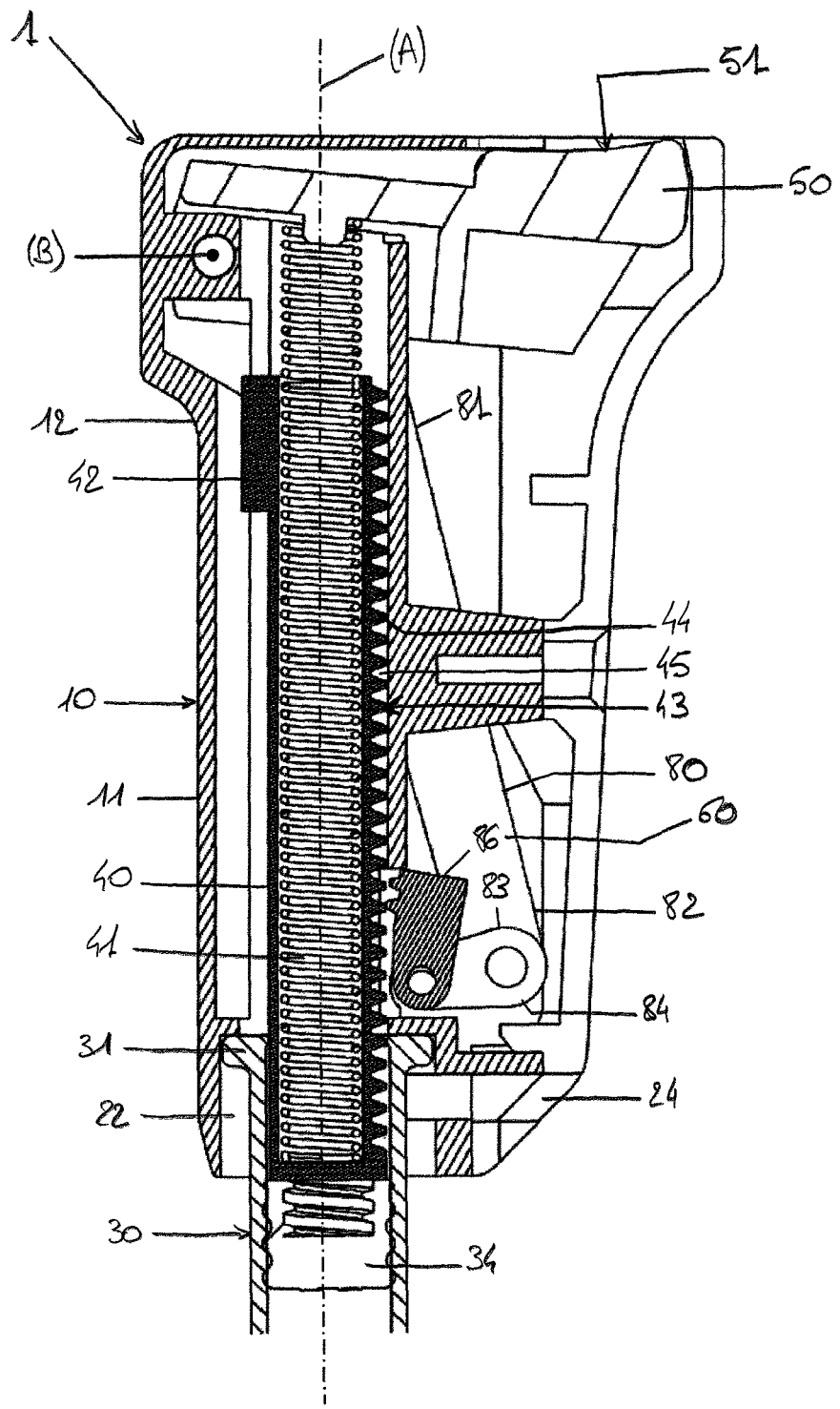
Figure 9B:
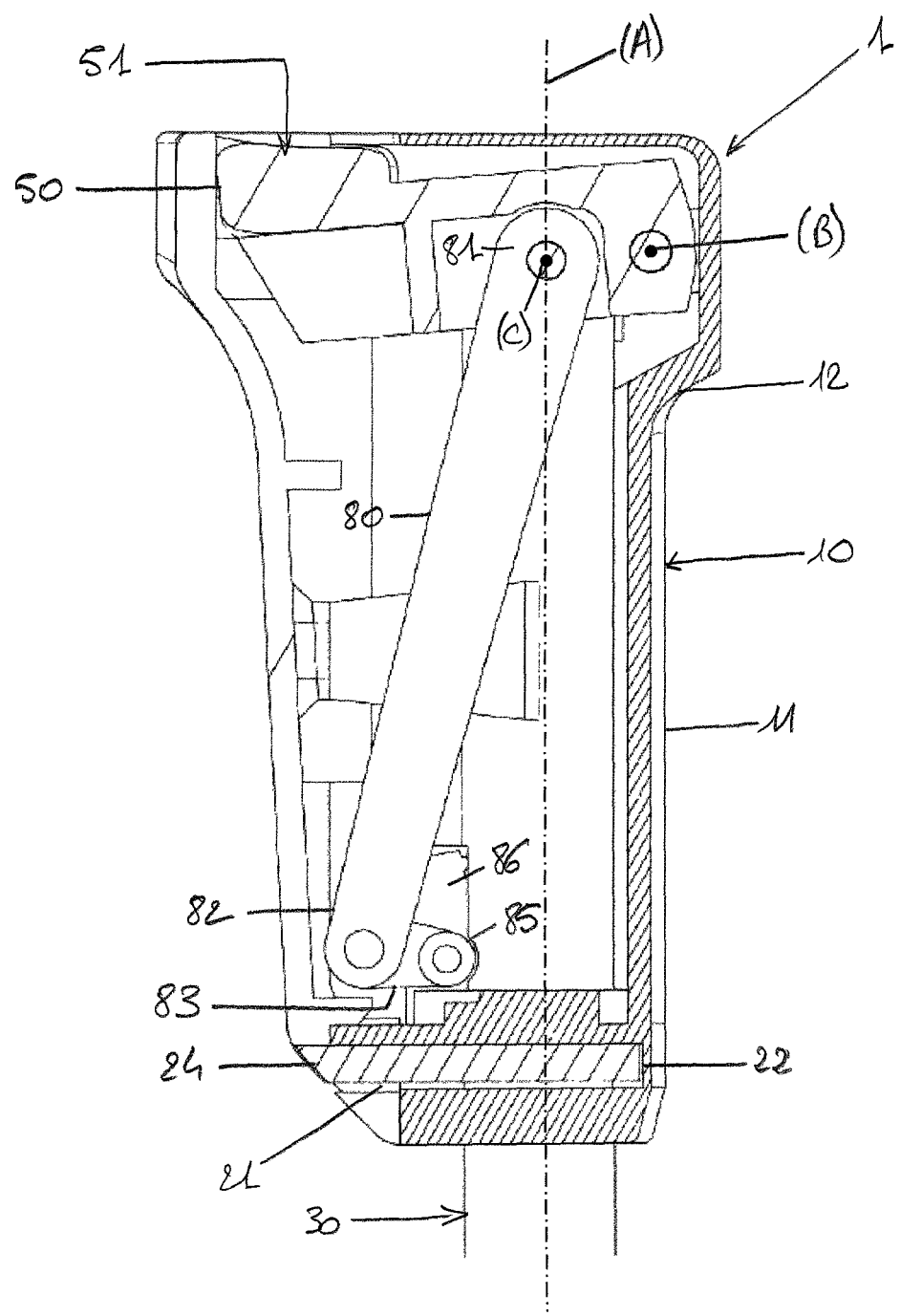
Figure 10:
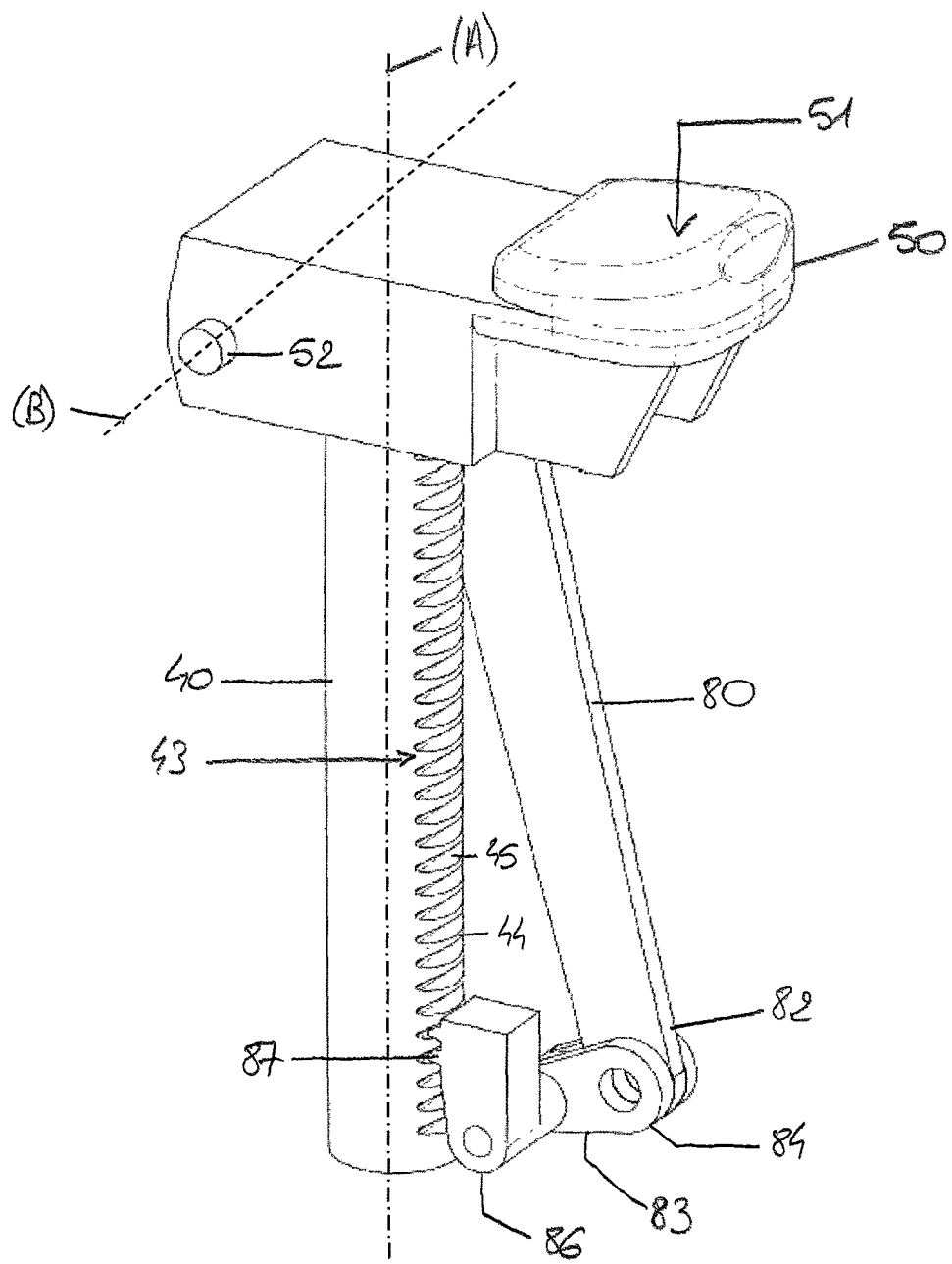
FIG. 10 is a perspective view of the selective blocking system of the injection device, according to the second embodiment.

As illustrated in FIGS. 8B and 9B, when the user pushes the actuation zone 51, the lever 50 moves in a tilting motion about the pivot axis (B) and pushes the connecting rod 80 in a distal direction. Due to the movement of the connecting rod 80, the secondary connecting rod 83 moves in a tilting motion about its connection 85 with the pawl 86. The pawl 86 disengages the toothed rack 43 of the piston rod 40 thus allowing the piston rod 40 to move translationally with the spring force of the spring 41 in a distal direction, to a distal operative position wherein the piston rod 40 engages the stopper 34 and pushes said stopper in the medical container 30. The composition is thus expelled from the medical container. In this position, the spring 41 is at least partially released.

As long as the user keeps pushing the actuation zone 51, the connecting rod 80 remains in a distal position, the pawl 86 remains disengaged from the toothed rack 43 of the piston rod 40, the piston rod 40 keeps moving in the distal direction with the release of the spring 41, and the injection continues.

During injection, when the user releases the actuation zone 51, the lever 50 moves back in a tilting motion to its rest position thanks to the spring force of the spring 41, the pawl 86 reengages the toothed rack 43 of the piston rod, and the device 1 returns in the rest situation described previously, the piston rod 40 being in a more distal position than previously.

As such, the user can start or stop the injection of the composition, simply by pressing the actuation zone 51 during a certain amount of time or releasing it.

Advantageously, when the pawl 86 disengages the toothed rack 43, the teeth 87 of the pawl 86 remain partially inserted into the notches 45 of the toothed rack 43 and abut sequentially the teeth 44 of the toothed rack as the piston rod 40 is moving, thanks to a return spring (not shown) provided in the connection between the pawl 86 and the secondary connecting rod 83. The abutment of the teeth 87 of the pawl 86 against the teeth 44 of the toothed rack 43 causes the piston rod 40 to be slightly slowed down and the injection rate to be decreased accordingly, as compared to a situation where no abutment between the teeth 87 of the pawl 86 and the teeth 44 of the toothed rack of the piston rod 40 occurs. As the user pushes the actuation zone 51 harder, the intensity of the abutment decreases and the injection rate increases accordingly, until a maximum wherein the teeth 87 of pawl 86 and the teeth 44 of the toothed rack 43 are totally separated. The user can thus adapt and vary the intensity of the abutment of the teeth 87 of the pawl against the teeth 44 of the toothed rack, simply by pushing the actuation zone 51 harder or lighter, thereby adjusting the speed of the piston rod 40 and the injection rate.

Moreover, as each abutment corresponds to the pitch of the toothed rack 43, which can be associated with a unitary dose of composition, the abutments help the user to control the quantity of injected composition by adjusting the number of unitary doses.

The abutment of the pawl 86 against the teeth 44 of the toothed rack 43 causes advantageously a corresponding sound for the user to be aware of the abutment.

Regardless the embodiment of the selective blocking system 60, at the end of the injection, the device may be reset by the user, by hand, so as to proceed to another injection. To do so, the empty medical container 30 is removed from the container holder system 20, by first removing the insert 24 when appropriate, and the piston rod 40 is pushed by the user in a proximal direction back to the proximal rest position while keeping the actuation zone 51 pushed. A new filled medical container 30 may then be positioned in the container holder system 20 and secured by the insert 24 when appropriate.

The pivot axis (C) of the stud 52 and the spring axis (A) are orthogonal and preferably intersect. In other terms, when the device is observed from a side, as illustrated in FIGS. 3A-B and 4A-B, and in the FIGS. 8A-B and 9A-B, the stud 52 is aligned with the piston rod 40.

In this configuration, according to the first embodiment, the force applied by the connecting rod 70 onto the wheel 75 along the friction surface, namely the brake force, corresponds substantially to the spring force.

Similarly, according to the second embodiment, the force applied by the pawl 86 onto the toothed rack 43 via the connecting rod 80, namely the brake force, corresponds substantially to the spring force.

Hence, the piston rod 40 is blocked as firmly as possible with the entirety of the spring force, and there is no risk of the piston rod 40 moving when the lever 50 is in the rest position.

Alternatively, the pivot axis (C) of the stud 52 and the spring axis (A) may not intersect, and the stud may not be aligned with the piston rod 40. In this configuration, the brake force is slightly inferior to the spring force, but sufficient to firmly block the piston rod 40.

When the lever 50 passes from the rest position to the second position, the piston rod 40 is moved by the spring force. Therefore, the force of the spring 41 is used for both moving and blocking the piston rod 40 so as to respectively start and stop the injection.

To illustrate the previous paragraph, the position $X_{Act}$ of the actuation zone 51, the position $X_B$ of the pivot axis (B), and the position $X_C$ of the pivot axis (C) are represented in FIG. 4A on an axis (X) orthogonal to the spring axis (A), and orthogonal to and intersecting the pivot axis (B) and the pivot axis (C). $X_{Act}$ is a projection in a direction parallel to the axis (A) of the central point of the actuation zone 51 on the axis (X). $X_B$ and $X_C$ are the intersecting points of the respective axes (B) and (C) with the axis (X).

The distance $D_{XAct-XC}$ between $X_{Act}$ and $X_C$ is greater than the distance $D_{XC-XB}$ between $X_C$ and $X_B$, along the axis (X). This induces a lever effect that allows the user to push the actuation zone 51 with a reduced force compared to the brake force.

The lever ratio LR is defined as follows:

$$LR = \frac{1}{\left|\frac{D_{XAct-Xc}}{D_{Xc-XB}}\right|}$$

It follows from this formula that the greater the distance $D_{XAct-XC}$ relatively to the distance $D_{XC-XB}$, the lower the lever ratio, and the greater the lever effect.

For example, with a distance $D_{XAct-XC}$ of 23.50 cm (centimeters) and a distance $D_{XC-XB}$ of 7.50 cm, the lever ratio LR is as follows: LR=1/(23.50/7.50), which is equal to about ⅓. In this case, when the lever is in the rest position, the spring 41 is blocked axially by the selective blocking system and the brake force is equal to the spring force. In order to carry out the injection of the composition, the user pushes the actuation zone 51 by applying a force equals to only one third of the brake force.

With a distance $D_{XAct-XC}$ of 20.50 cm and a distance $D_{XC-XB}$ of 10.5 cm, the lever ratio LR is as follows: LR=1/(20.50/10.50), which is equal to about ½.

In this case, in order to carry out the injection of the composition, the user pushes the actuation zone 51 by applying a force equals to only half of the brake force.

Hence, for carrying out the injection, the force that the user has to apply onto the actuation zone 51 is strongly reduced compared to the brake force. As a consequence, the device 1 of the disclosure allows at the same time:

to use a spring 41 with a high spring force so as to be able to carry out the injection of viscous compositions while helping the user with a reduced physical strength, and to provide a total blocking of said spring 41 and the piston rod 40.

The invention claimed is:

1. An assisted injection device for injecting a composition contained in a medical container, comprising:
    a body configured to receive the medical container in a fixed position relative to the body,
    a spring-loaded piston rod translationally movable inside the body along a spring axis, between a proximal rest position and a distal operative position wherein the piston rod engages a stopper of the medical container and pushes the stopper in the medical container,
    a lever pivotably mounted on the body about a first pivot axis orthogonal to the spring axis at a first distance from the spring axis, comprising an actuation zone configured to be directly pressed on by a user, said actuation zone being opposite the first pivot axis relative to the spring axis, at a second distance from the spring axis, and
    a selective blocking system coupled to the lever by a second pivot axis orthogonal to the spring axis,
    the lever being pivotable between a rest position wherein the selective blocking system engages the piston rod to prevent any translational movement of the piston rod and a second position wherein the selective blocking system releases the piston rod to allow the piston rod to move toward the distal operative position under the spring force.

2. The assisted injection device according to claim 1, wherein the second distance is greater than the first distance.

3. The assisted injection device according to claim 1, wherein the second pivot axis intersects the spring axis.

4. The assisted injection device according to claim 1, wherein the piston rod is provided with a toothed rack that extends along its outer wall, and the selective blocking system comprises:
    a rotatably movable wheel comprising:
    a first part being a rotatably movable cogwheel, including teeth adapted to mesh with the toothed rack of the piston rod,
    a second part coaxial with the first part and rotatably movable with the first part, comprising a curved surface, and
    a connecting rod including a first end coupled to the lever by the second pivot axis and a second end provided with a hole that receives the second part of the wheel, the connecting rod being movable by the lever between a first position wherein the lever is in the rest position and the inner surface of the hole engages the curved surface of the second part of the wheel so as to block the wheel by friction thereby blocking the piston rod, and a second position wherein the lever is the operative position and the inner surface of the hole disengages the curved surface of the second part of the wheel so as to allow the rotation of the wheel thereby allowing the piston rod to move.

5. The assisted injection device according to claim 4, wherein the ratio of the diameter of the first part of the wheel to the diameter of the second part of the wheel is between 2 and 3.

6. The assisted injection device according to claim 4, wherein the curved surface of the second part of the wheel is made of a material selected from the group consisting of epoxy resin, plastic material, steel, aluminum, or rubber and the inner surface of the hole of the connecting rod is made of a material selected from the group consisting of epoxy resin, plastic material, steel, or rubber.

7. The assisted injection device of claim 4, wherein the curved surface of the second part of the wheel is made of at least one of epoxy resin, plastic material, steel, aluminum, or rubber and the inner surface of the hole of the connecting rod is made of at least one of epoxy resin, plastic material, steel, or rubber.

8. The assisted injection device according to claim 1, wherein the piston rod is provided with a toothed rack that extends along its outer wall, and the selective blocking system comprises:
   a pawl comprising a surface provided with a at least one tooth, and
   a connecting rod assembly including a first end coupled to the lever by the second pivot axis, and a second end coupled to the pawl, the connecting rod assembly being movable by the lever between a first position wherein the lever is in the rest position and the pawl meshes with the toothed rack of the piston rod so as to block the piston rod, and a second position wherein the lever is in the operative position and the pawl disengages the toothed rack of the piston rod so as to allow the piston rod to move.

9. The assisted injection device according to claim 1, wherein the body comprises a container holder system configured to receive at least a portion of the medical container and to hold the medical container aligned with the movement direction of the piston rod so that when moving from the proximal rest position to the distal operative position, the piston rod engages the stopper of the medical container and pushes the stopper in the medical container to inject the composition.

10. The assisted injection device according to claim 9, wherein the container holder system comprises:
    an opening provided in the distal wall of the body that leads to a housing adapted to receive at least a portion of the medical container in a position aligned with the movement direction of the piston rod,
    a slot provided in the outer wall of the body that leads to the housing, and
    an insert adapted to be inserted in the slot to contact the medical container and to maintain the medical container in a fixed position in the housing.

11. The assisted injection device according to claim 9, wherein the container holder system comprises:
    a slot provided in the outer wall of the body that leads to a housing, configured to receive at least a portion of the medical container and to maintain the medical container in a fixed position aligned with the movement direction of the piston rod, and
    a through groove provided in the distal wall of the body, continuous with the slot and extending in the distal wall from the slot, the groove being configured to guide the medical container inserted via the slot to the housing.

12. The assisted injection device of claim 1, wherein said device is handheld.

13. The assisted injection device of claim 1, wherein the second distance is at least two times greater than the first distance.

* * * * *